United States Patent
Smith

(10) Patent No.: US 6,365,153 B2
(45) Date of Patent: Apr. 2, 2002

(54) MECHANICALLY ELONGATED NEURONAL CELLS AND METHODS FOR PRODUCING AND USING THESE CELLS

(76) Inventor: Douglas H. Smith, 21 Hunt Meet Rd, Concord/Boothwyn, PA (US) 19061

( * ) Notice: Subject to any disclaimer, the term of this patent is extended or adjusted under 35 U.S.C. 154(b) by 0 days.

(21) Appl. No.: 09/800,395

(22) Filed: Mar. 6, 2001

Related U.S. Application Data

(62) Division of application No. 09/630,461, filed on Aug. 2, 2000.
(60) Provisional application No. 60/149,408, filed on Aug. 17, 1999.

(51) Int. Cl.$^7$ .......................... A01N 63/00; A01N 65/00
(52) U.S. Cl. ...................... 424/93.7; 424/93.1; 424/520; 424/422; 424/423; 435/325; 435/410; 435/41; 435/1.1
(58) Field of Search .............................. 424/93.7, 93.1, 424/520, 422, 423; 435/325, 410, 41, 1.1

(56) References Cited

PUBLICATIONS

Björklund et al., "Cell Suspension Grafts of Noradrenergic Locus Coeruleus neurons in Rat Hippocampus and Spinal Cord:Reinnervation and Transmitter Turnover", 1986 *Neuroscience* 18:685–698.
Buchanan et al, "Transplants of Embryonic Brainstem Containing the Locus Coeruleus into Spinal Cord Enhance the Hindlimb Flexion Reflex in Adult Rats", 1986 *Brain Res.* 381:225–236.
Galbraith et al., "Shear Stress Induces Spatial Reorganization of the Endothelial Cell Cytoskeleton", 1998 *Cell Motil. Cytoskel.* 40:317–330.
Hiraoka et al., "The Use of a Charge–Coupled Device for Quantitative Optical Microscopy of Biological Structures", 1987 *Science* 238:36–41.
Lamoureux et al., "Direct evidence that growth cones pull", 1989 *Nature* 340:159–162.
McDonald J.W., "Repairing the Damaged Spinal Cord", 1999 *Sci. Amer.* 281:64–73.
Moorman et al., "A neurotransmitter specific functional recovery mediated by fetal implants in the lesioned spinal cord of the rat", 1990 *Brain Res.* 508:194–198.
Munir et al., "Excitotoxic Cell Death and Delayed Rescue in Human Neurons Derived from NT2 Cells", 1995 *J. Neurosci.* 15:7847–7860.
Pleasure et al., "Pure, Postmitotic, Polarized Human Neurons Derived from NTera 2 Cells Provide a System for Expressing Exogenous Proteins in Terminally Differentiated Neurons", 1992 *J. Neurosci.* 12:1802–1815.
Pleasure et al., "NTera 2 Cells:A Human Cell Line Which Displays Characteristics Expected of a Human Committed Neuronal Progenitor Cell", 1993 *J. Neurosci. Res.* 35:585–602.
Ribotta et al., "Transplantation of embryonic noradrenergic neurons in two models of adult rat spinal cord injury:ultrastructural immunocytochemical study", 1996 *Brain Res.* 707:245–255.
Shirinsky et al., "Mechano–chemical Control of Human Endothelium Orientation and Size", 1989 *J. Cell Biol.* 109:331–339.
Smith et al., "High Tolerance and Delayed Elastic Response of Cultured Axons to Dynamic Stretch Injury", 1999 *J. Neurosci.* 19:4263–4269.
Stichel et al., "Experimental Strategies to Promote Axonal Regeneration After Traumatic Cental Nervous System Injury", 1998 *Prog. Neurobiol.* 56:119–148.
Yano et al., "Cyclic Strain Induces Reorganization of Integrin $\alpha_5\beta_1$ and $\alpha_2\beta_1$ in Human Umbilical Vein Endothelial cells", 1997 *J. Cell. Biochem.* 64:505–513.
Zheng et al., "Tensile Regulation of Axonal Elongation and Initiation", 1991 *J. Neurosci.* 11:1117–1125.
Zompa et al., "Transplant Therapy:Recovery of Function after Spinal Cord Injury", 1997 *J. Neurotrauma* 14:479–506.

*Primary Examiner*—Leon B. Lankford, Jr.
*Assistant Examiner*—Brett Ozga
(74) *Attorney, Agent, or Firm*—Licata & Tyrrell P.C.

(57) ABSTRACT

Mechanically elongated neuronal cells and methods of mechanically producing elongated cells are provided. Also provided are methods for transplanting elongated neuronal cells into an animal for treatment of spinal cord injuries and other nerve injuries.

3 Claims, 4 Drawing Sheets

MECHANICALLY ELONGATED NEURONAL CELLS AND METHODS FOR PRODUCING AND USING THESE CELLS

This application is a divisional of U.S. application Ser. No. 09/630,461 filed Aug. 2, 2000 which claims the benefit of provisional U.S. application Ser. No. 60/149,408 filed Aug. 17, 1999.

INTRODUCTION

This invention was supported in part by funds from the U.S. government (NIH Grant No. AG12527) and the U.S. government may therefore have certain rights in the invention.

BACKGROUND OF THE INVENTION

In the United States, approximately 12,000 people each year suffer some form of spinal cord injury (SCI), with over 200,000 people chronically paralyzed from SCI. Current therapy for SCI includes surgery, drug treatment and prolonged rehabilitation. However, due to the extensive loss of neural tissue and the poor regenerative capacity of such tissue, the success of current therapy has been limited. The injury of concern is the loss of continuity of bi-directional nerve signals between the brain and the extremities. In most SCIs, the lesioned region of the spinal cord reaches several centimeters in length. Therefore, natural reconnection in these cases is an extremely unlikely event.

Methods for transplantation of neural tissue into the area of the SCI in order to reduce the deficits associated with the injury and to promote functional recovery are currently under development. In animal studies, embryonic tissue transplants into the areas of a lesioned spinal cord have been shown to survive and to reinnervate certain regions of the spinal cord (Bjorklund et al. 1986. *Neuroscience* 18:685–698; Buchanan and Nornes. 1986. *Brain Res.* 381:225–236; Moorman et al. 1990. *Brain Res.* 508:194–198; Ribotta et al. 1996. *Brain Res.* 707:245–255). Such studies have shown that the time of transplant after injury and the type of cell transplanted affects the success of the attempted transplant. These transplant studies have focused on reinstating nerve fiber connections using ex vivo donor material or attempting to grow long nerve fibers by attractant molecules. However, neither approach to transplantation has had success in growing nerve fibers over a distance of more than a few millimeters.

A variety of methods have been used as a way to bridge or fill spinal cord injury lesions that include transplanting peripheral nerves, transplanting intact fetal spinal cords, transplanting progenitor cells, transplanting stem cells, or transplanting dissociated cells from nervous tissue (McDonald, J. W. 1999. *Sci. Amer.* 281:64–73; Zompa, E. A. et al. 1997. *J. Neurotrauma* 14:479–506). Some of these techniques have resulted in improved functional outcome in animal models of spinal cord injury. However, improved function has not been attributed directly to the reinstatement of spinal cord signals through the transplant. Rather, it has been proposed that the primary benefit of the transplanted tissue in these models is through physical and biochemical support for the host tissue surrounding the lesion (Stichel, C. C. and H. W. Muller. 1998. *Prog. Neurobiol.* 56:119–148; Anderson, D. K. et al. 1995. *Brain Pathol.* 5:451–457). While the results of these studies have been promising, the goal of re-establishing an axonal connection through a spinal cord lesion has yet to be realized.

Studies have shown that short-term tension on single axon growth cones from chick sensory neurons resulted in "towed growth" (Bray, D. 1984. *Develop. Neurobiol.* 102:379–389; Lamoureux, P. et al. 1989. *Nature* 340:159–162; Zheng, J. et al. 1991. *J. Neurosci.* 11:1117–1125). Though poorly understood, it is believed that this growth mechanism commonly occurs in synapsed CNS axons during embryogenesis and development. Since tracts of synapsed axons have no growth cones from which to extend to match the growth of an organism. Axon elongation must occur from reorganizing and building onto the center length of the axon. It is possible that continuous tensile forces along axons trigger this growth in length.

Elongation of cells used for transplant would therefore be advantageous. Studies with other types of cells have shown that mechanical methods can be used to stretch cells. For example, research on human endothelial cells has shown that mechanical stretching of these cells results in changes in cell orientation and size, as well as cell morphology and function (Yano et al. 1997. *J. Cell. Biochem.* 64:505–513; Shirinsky et al. 1989. *J. Cell Biol.* 109:331–339; Galbraith et al. 1998. *Cell Motil. Cytoskel.* 40:317–330). In one study, mechanical stretching of neuronal cells demonstrated the high tolerance of these cells to dynamic stretch injury (Smith et al. 1999. *J. Neurosci.* 19:4263–4269). The focus of studies on elongation of cells through mechanical stretching, however, has been on the degree of stretch that can be tolerated before cells lose function or the ability to recover from injury and possible use of these cells in a cell injury model.

It has now been found that mechanically stretched neuronal cells can be produced and used to reconnect damaged spinal cord tissue and reinstate flow of nerve signals.

SUMMARY OF THE INVENTION

An object of the present invention is to provide compositions comprising mechanically elongated neuronal cells.

Another object of the present invention is to provide a method for producing elongated cells which comprises culturing selected cells, plating said cultured cells onto an overlying membrane and an underlying membrane so that said cultured cells cover both membranes, and moving the overlying membrane across the underlying membrane via a motor-driven movement so that the cultured cells are mechanically stretched and split into two populations connected by elongated cells. In a preferred embodiment, this method is performed on neuronal cells such as N-tera2 cells.

Yet another object of the present invention is to provide a method for treating nerve injury which comprises transplanting elongated neuronal cells into the nerve of an animal suffering from a nerve at the site of injury. This method would include treatment of spinal cord injury.

DETAILED DESCRIPTION OF THE INVENTION

The primary functional constituents of the spinal cord are myelinated axons and neurons. Signals travel from brain to body and back via these axons which synapse to spinal neurons communicating with the targeted body region. Paralysis develops when the bi-directional signaling is interrupted due to axon damage which severs communication below the site of injury. A key to recovery from such injury would be axonal transplantation. However, axons, which grow out of neurons and then are guided to adjacent neuronal cells by chemical attractants, have not been able to be grown over the distances required for SCI, distances of centimeters rather than millimeters.

A mechanical device has now been developed to elongate neuronal cells so that two populations of neurons can be connected by stretching axonal cells over distances not possible with other prior art methods. Although previous studies have shown that axons exhibit short-term tolerance to strain or stretching, the ability of axonal cells to tolerate long-term stretch and then to elongate successfully and remain viable has not previously been shown.

Figure 1:
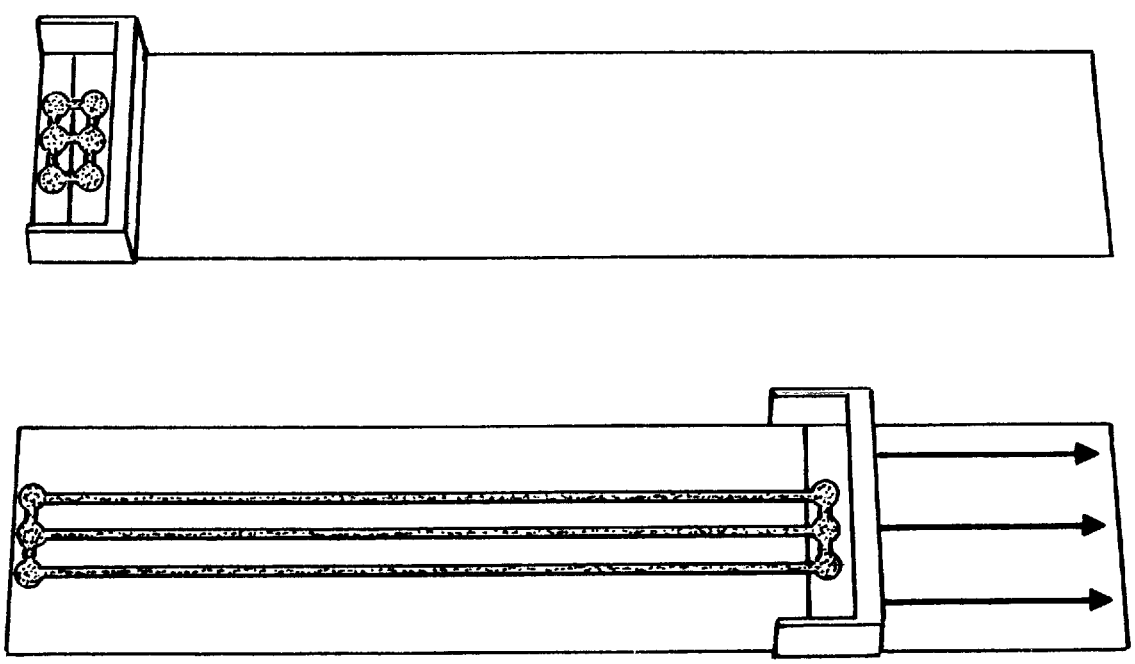
FIG. 1 provides a diagram of the process of axonal "stretch-induced growth". In the top picture, a short membrane attached to an aluminum block is placed on top of a long rectangular membrane. These structures are enclosed in a Plexiglas box with a gas exchange port (not shown). A chamber is formed by the aluminum block in which mammalian CNS neurons are plated and allowed to integrate over 3 days. A neural network is formed, including axons that grow across the border between the top and bottom membranes. In the bottom picture, movement of the aluminum block is depicted via a computer controlled microstepper motor system that divides the culture and progressively separates the opposing halves by sliding the top membrane across the bottom membrane at a step-rate of 3.5 micrometers every 5 minutes. This technique results in the stretch-induced growth of fascicular tracts of axons spanning the two membranes.

To elongate cells, an enclosed cell culture system was developed which comprises a plexiglass box with a removable lid and glass bottom and a gas exchange port. On the inside base, a long rectangular absorbable membrane (substrate; Lactosorb, BioMet, Inc., Warsaw Ind.) for neuron attachment was fixed in place. The biologically absorbable material was chosen as it is more compatible for transplantation into tissue. Another shorter membrane was placed on top leaving an exposed region of the underlying membrane near one end (see FIG. 1). This overlying membrane was fixed to a movable bar that was driven by two steel rods. Movement of the overlying membrane across the underlying membrane was performed by activation of a motor-table assembly (Servo Systems, Inc., Montville, N.J.) and microstepper motors (Pacific Scientific, Rockford, Ill.). Control of the movements was computer driven using a linear table (Aerotech, Irvine, Calif.), an encoder (Remco Encoders, Inc., Goleta, Calif.) and an indexer/driver (Panther, Intelligent Motor Systems, Marlborough, Conn.; QuickStep II Driver Software).

Any cells can be elongated with this device. By "elongated cells" it is meant cells that have been modified so that they have an increased length as compared to cells that have not been stretched with the method of the present invention. In a preferred embodiment of the present invention, the device is used to produce compositions comprising elongated neurons. In addition to the elongated cells, the compositions may further comprise culture media and selected growth factors. Neurons to be elongated can be derived from various animal sources, including humans, and isolated via filtration. Alternatively, neuronal cell lines such as the N-tera2 cell line can be elongated. Using this device, it has been shown that the axons or neurons can be elongated to greater than 0.2 cm after one day of stretching and greater than 1 cm after 5 days of stretching.

Figure 2:
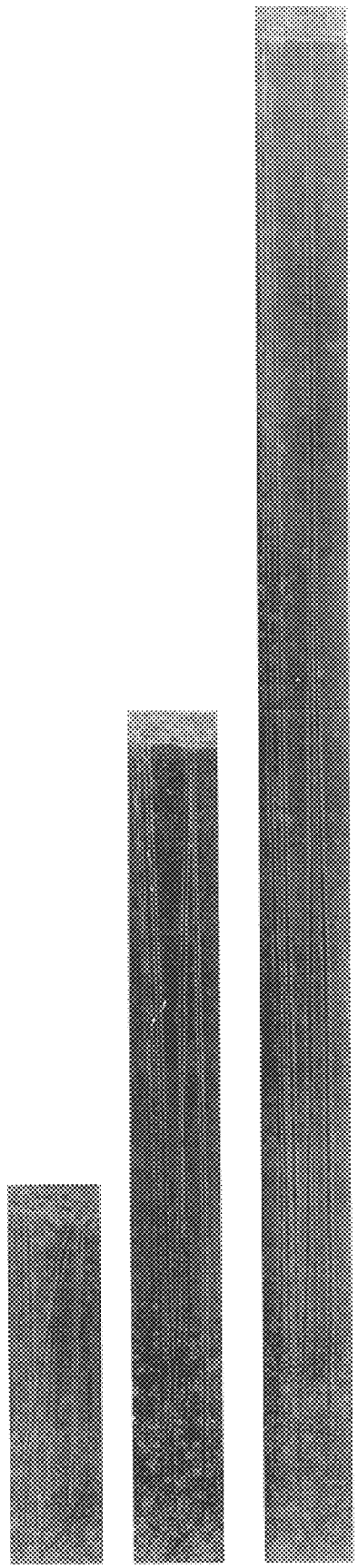
FIG. 2 depicts phase photomicrographs demonstrating stretch-induced growth of integrated CNS axons. The same region of a progressively expanding live culture is shown at 2 days (top), 4 days (middle) and 7 days (bottom) of elongation. At each end are the parent and target neurons adhering to the bottom membrane (right) and top membrane (left). Spanning these neurons are large bundles of progressively elongated axon tracts. Bar represents 1 mm.
Figure 3:
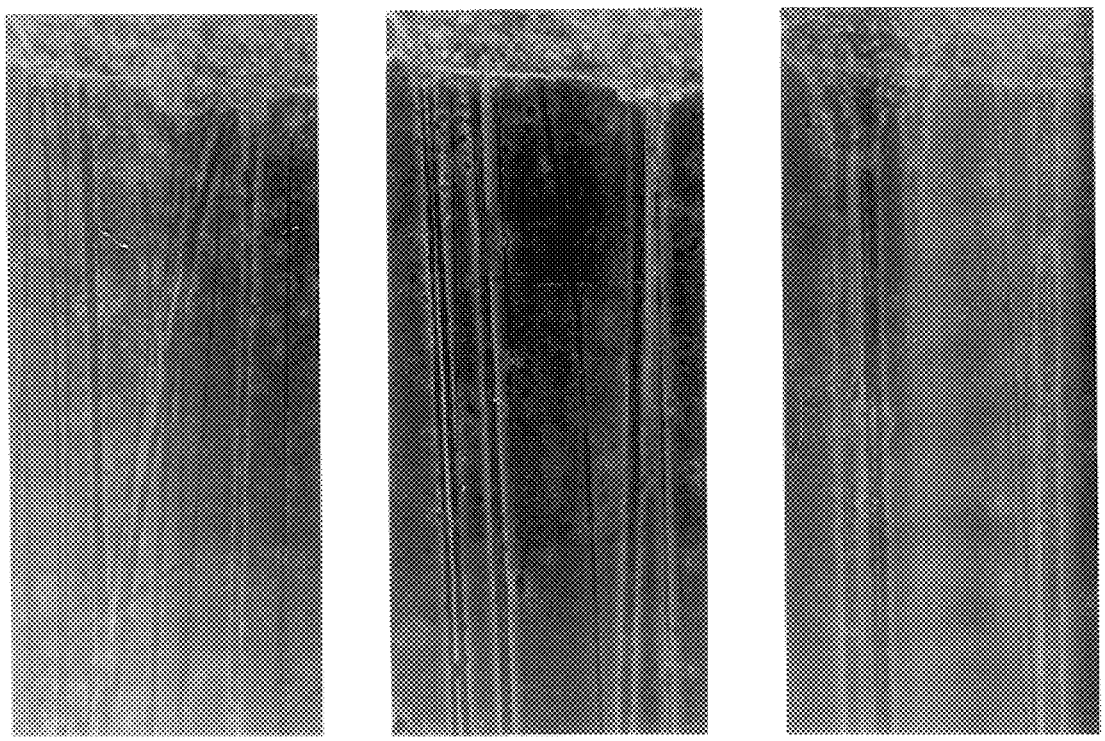
FIG. 3 depicts phase photomicrographs of one region of stretch-grown axons at the border of the top membrane at 2 days (left), 4 days (middle) and 7 days (right) of elongation. Note the gradual joining of neighboring axon bundles and thickening of the bundles at the edge of the top membrane. Bar represents 50 microns.
Figure 4:
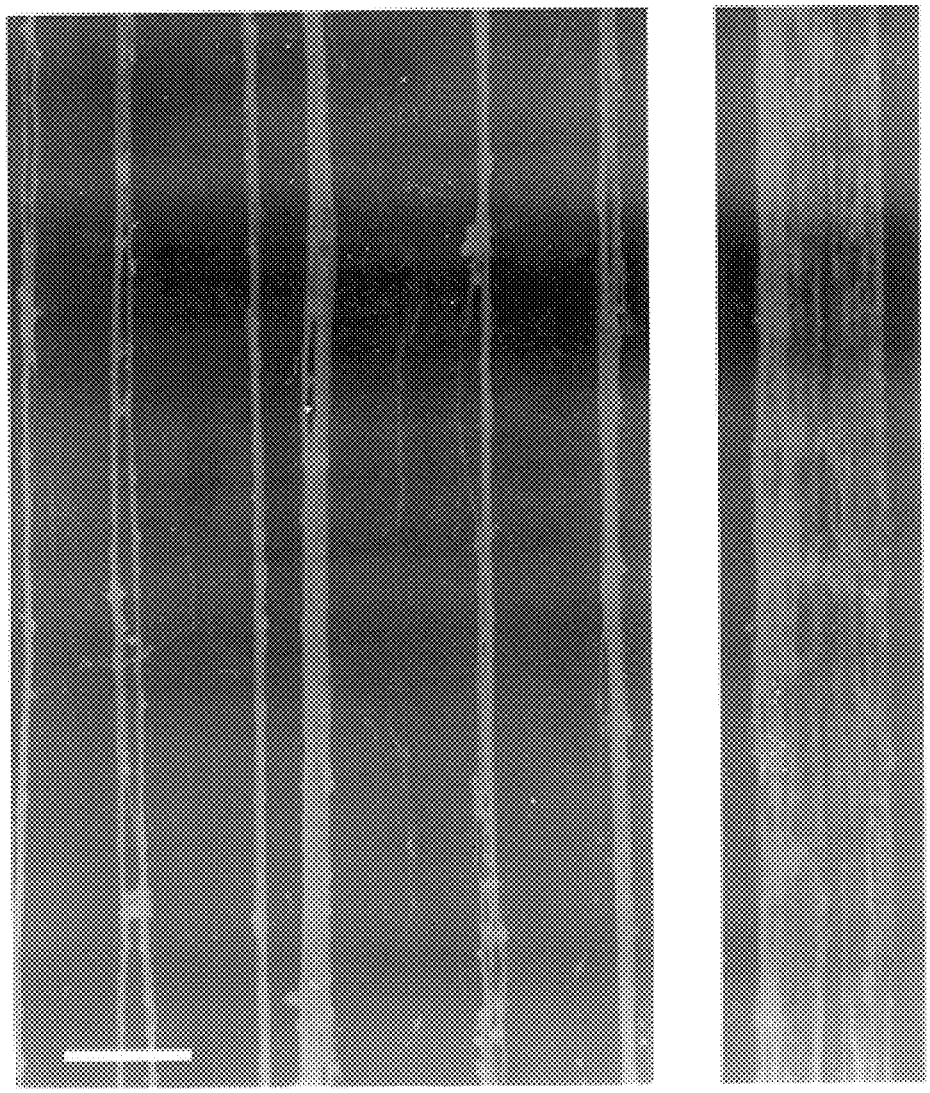
FIG. 4 depicts representative fluorescence photomicrographs of axon tracts at 7 days of stretch-induced growth, elucidated by immunostained microtuble protein in fixed cultures. On the left are multiple long fascicular axon tracts arranged in parallel that were produced by stretch-induced growth (bar=50 microns). On the right is a slightly enlarged view of a large 40 micron fascicular axon tract demonstrating a substantial network of microtubules.

The ability of this device to elongate neurons was demonstrated using the N-tera2 cell line and primary rat neurons. Cells (approximately 10 million) were plated over the outside border of the overlying and underlying membrane. The cells remained in culture for three to seven days to allow time for adherence of neurons to the membrane and for the growth of nerve fibers (axons and dendrites), forming a network between the neurons. Accordingly, a single neuron network was established that covered both the overlying and underlying membranes. The driver of the device was then activated and the stepper motors moved the top (overlying) membrane across the underlying membrane at speeds of 3.5 to 7 $\mu$m every 5 minutes or 1 to 2 mm/day (see FIG. 1). The movement of the membrane split the neuron culture into two populations, bridged by bundles of axons (see FIG. 2). The axons readily adapted to the stretch even to distances of over one centimeter (see FIGS. 3 and 4).

Using the step rate of 3.5 $\mu$m per 5 minutes to progressively move further apart the two halves that had been formed with stretching, it was found that few of no neuronal somata were present in the expanding center region. However, bridging this expanding center region were numerous large bundles of axoms, 3 to 40 $\mu$m in diameter. These bundles originated from fascicular tracts of axons that had crossed the dividing line between the underlying and overlying membranes prior to separation. While these tracts had random directional orientations prior to stretching with the method of the instant invention, the axon bundles crossing the expanding gap gradually assumed straight orientations arranged in parallel (see FIG. 4). These bridging axons appeared to readily adapt to stretch event though they had increased their original length or 100 to 200 $\mu$m to become longer than 7 mm over 7 days of stretch-growth. These bridging axons grew in girth as well as in length. In particular, the hillocks of the axon bundles at the edges of the neuronal populations became wider during elongation (see FIG. 3). In addition to general thickening, there was a joining together of neighboring axon bundles during stretch-growth. Thus, there were progressively fewer but much broader fasicular tracts of axons bridging the two populations of neurons. With the typical diameter of the axons at less than 1 $\mu$m, the larger bundles were estimated to contain more than 1000 axons. Despite the relatively rapid stretch-growth of these axons, when the flasks containing the cells were agitated, lateral movement of the axon bundles was observed, indicating that there remained some slack in the axon bundles and that the center portion of the axon bundles was not attached to the membranes. The regions of the bundles nearest the ends of the gaps, however, did appear to adhere to the underlying membrane.

These results are the first demonstration of substantial progressive growth of large tracts of synapsed CNS axons in response to a continuous mechanical tension. Further, these data show for the first time that mechanically elongating axon bundles consolidate into larger tracts. Moreover, the elongated axon/neuron cultures remained sufficiently viable for use as transplant material. Although these studies were terminated at 7 days of stretch-growth, these was no indication that further elongation could not be achieved with longer times of stretch-growth.

Doubling of the elongation speed from 3.5 $\mu$m/5 minutes to 7 $\mu$m/5 minutes led to an almost total obliteration of the axon bundles, with only a few remaining that spanned the gap at 3 days of stretch. Therefore, there is a limit to the tolerance of long-term stretch in terms of the rate of stretch, which is lower than the tolerance previously reported for short-term elongation of single axons towed from their growth cones.

Compositions comprising elongated neuronal cells of the present invention are useful as a source of transplant material for patients with SCI as well as other nerve lesions. Methods for transplantation of the cells produced by the method of the instant invention are well known to those of skill in the art of cell transplantation.

In one embodiment, mechanically elongated neurons are implanted at both ends of a lesion proximate to viable cells so that the implanted cells can replace nerve function and reconnect nerves of the individual to remedy or otherwise ameliorate the injury. The neurons are implanted in a location that allows processes which develop therefrom to substitute for the processes of the damaged nerve, thereby repairing the damaged nerve network. Thus, as used herein, the term "at or near a site of said nerve damage" is meant to refer to the location where nerve cells are implanted in order to replace destroyed, damaged or dysfunctional nerve cells and/or restore function resulting from destroyed, damaged or dysfunctional nerve cells. The location is defined as being a site where such implanted cells can develop as replacement cells for destroyed, damaged or dysfunctional nerve cells and make the necessary linkages to restore function lost due to destroyed, damaged or dysfunctional nerve cells.

A transplant strategy is to match the length of the stretched axon cultures with the length of the spinal cord lesion. Transplant would proceed by placing the membrane with the cultured cells into the lesion so that neurons at both ends of the axon bundles are in proximity to viable tissue at the end margins of the spinal cord lesion. In addition to spinal cord repair, the transplant material can be used as a bridge for other types of neural injuries, including optic nerve damage and peripheral nerve damage. Transplant of elongated axons for peripheral nerve damage repair may be most optimal due to the more permissive neural growth environment in the peripheral nervous system compared with the CNS.

The capacity of grafted elongated neurons to promote axonal regeneration and functional recovery in vivo can be demonstrated using an animal model of spinal cord injury. For example, adult rats can be surgically anesthetized and prepared for aseptic surgery. For these studies, rats are first trained in the "staircase test" to assess forepaw function prior to receiving a C3–C4 laminectomy and cervical cord hemisection, which causes loss of function in one upper limb. Immediately following the hemisection, into one group of animals is transplanted a membrane with the elongated axons stretched to the length of the lesion. The membrane with the elongated axons stretched to the length of the lesion is then transplanted so that the neuron populations at each end of the membrane are inserted into viable tissue at each end of the lesion. The second group of animals is left untreated as controls.

Beginning at one week post-transplant, the dorsal spinal cord is examined electrophysiologically to determine whether communication between proximal and distal regions of the lesion had been re-established.

Skilled forelimb function is also assessed using a staircase apparatus consisting of a plastic box with built-in left and right staircases with five steps each. The staircases are separated from each other in such a manner that it is impossible for an animal to reach the right staircase with any limb other than the right forelimb and vice versa. The five steps on each staircase are loaded with small food pellets, and the animals are allowed to acquire as many food pellets as possible using each forelimb independently in a 15 minute period. The number of pellets consumed by the rat are counted at the end of each test period and recorded as "number of pellets taken". Each animal is assessed in the staircase test preoperatively and at 1-, 4-and 8-weeks post-implant. At 8-weeks post-implant, animals are sacrificed and sections of the spinal cord are processed for serotonin (5-HT) immunohistochemistry to identify descending serotonergic fibers.

Similar transplant procedures can be performed in humans. For example, N-Tera2 cells are currently being evaluated for transplantation into the brain in human stroke patients. Prior to transplant, it is preferable to diagnose location and presence of any damage to the spinal cord and the volume of the damage by MRI and CT. Neuronal cells for implant are elongated as discussed above. It is preferred that a volume of cells equal to that of the damaged regions of the spinal cord be elongated. The surgeon then locates the appropriate level(s) of the spine and accesses the spinal canal to remove the damaged regions and other debris which might block nerve regeneration, using known techniques. Next the surgeon places the membrane of elongated neuronal cells into this region so that the elongated axons bridge the length of the lesion and the neuron populations at each end of the membrane are inserted into viable tissue at each end of the lesion. Next the layers surrounding the spinal cord are closed, as are the more superficial layers. In circumstances of the acute application of this technique following trauma, methylprednisolone is administered at the beginning of the surgery in the usual spinal injury dose and is continued for as long as the surgeon considers necessary, which may vary from 1 week to several months. In circumstances in which the cells are histocompatible with the recipient, or other situations under the physician's determination, anti-rejection therapy may not be needed.

The following nonlimiting examples are provided to further illustrate the present invention.

EXAMPLES

Example 1

CELL CULTURE

The N-tera2 cell line was selected because of the well-characterized ability of this cell line to differentiate into robust human neurons (Pleasure et al. 1992. *J. Neurosci.* 12:1802–1815; Pleasure, S. J. and Lee, V. M. J. 1993. *J. Neurosci. Res.* 35:585–602). In addition, this cell line has been shown to respond to excitatory injury in a manner similar to that of primary neuronal cell cultures (Munir et al.

1995. *J. Neurosci.* 15:7847–7860). The NT2 cells were maintained in culture with OptiMEM (Life Technologies, Gaithersburg, Md.) media supplemented with 5% fetal bovine serum (FBS; HyClone, Logan, Utah) and 1% penicillin-streptomycin (Pen-Strep; Life Technologies). To differentiate the NT2 cells into neurons (NT2N), the NT2 cells were cultured for 5 weeks in DMEM supplemented with 10% FBS (HyClone), antibiotics (1% Pen-Strep; Life Technologies), and 10 $\mu$M retinoic acid (Sigma, St. Louis, Mo.). To isolate neurons in the culture, the cells were trypsinized, triturated with a fire-polished Pasteur pipette, and replated in DMEM supplemented with 5% FBS and mitotic inhibitors (10 $\mu$M 5-fluoro-2'-deoxyuridine, 10 $\mu$M uridine, and 1 $\mu$M cytosine $\beta$-arabino-furanoside; Sigma) for 9 days. The cells remaining after this procedure have been determined to be 99% neuronal. The NT2N neurons were seeded on the absorbable membrane of the device and cultures were maintained in conditioned media (50% media from the first replate and 50% DMEM with 5% FBS).

Example 2

Microscopic Examination of Elongated Cells

Phase microscopy and photomicrography were performed on a Nikon Diaphot microscope with a Nikon 8008 camera. Confocal microscopy was performed with a Zeiss LSM5 (Heidelberg, Germany). Deconvolution microscopy as described by Hiraoka et al. 1987. *Science* 238:36–41 was performed on a Zeiss Axiovert 100 microscope equipped with a cooled CCD (Princeton Instruments (Trenton, N.J.) and DeltaVision constrained iterative deconvolution software (Applied Precision, Issaquah, Wash.).

What is claimed is:

1. A method for producing elongated cells comprising:
   (a) culturing selected neuronal cells;
   (b) plating the cultured cells onto an overlying membrane and an underlying membrane so that the cultured cells cover both membranes; and
   (c) moving the overlying membrane across the underlying membrane so that the cultured cells are mechanically stretched and split into two populations connected by elongated cells.

2. A method for treating nerve injury in an animal comprising transplanting into a nerve of an animal suffering from a nerve injury a composition comprising integrated elongated neuronal cells resulting from ex vivo machine-driven, physical stretching of already synapsed neurons maintained in culture.

3. A method for treating spinal cord injury in an animal comprising transplanting into a spinal cord of an animal suffering from a spinal cord injury a composition comprising integrated elongated neuronal cells resulting from ex vivo machine-driven, physical stretching of already synapsed neurons maintained in culture.

* * * * *